United States Patent
Pomper et al.

(10) Patent No.: US 10,232,058 B2
(45) Date of Patent: Mar. 19, 2019

(54) PROSTATE-SPECIFIC MEMBRANE ANTIGEN-TARGETED PHOTOSENSITIZERS FOR PHOTODYNAMIC THERAPY

(71) Applicant: THE JOHNS HOPKINS UNIVERSITY, Baltimore, MD (US)

(72) Inventors: Martin G. Pomper, Baltimore, MD (US); Ronnie Mease, Fairfax, VA (US); Ying Chen, Lutherville-Timonium, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 72 days.

(21) Appl. No.: 15/029,188

(22) PCT Filed: Oct. 14, 2014

(86) PCT No.: PCT/US2014/060461
§ 371 (c)(1),
(2) Date: Apr. 13, 2016

(87) PCT Pub. No.: WO2015/057692
PCT Pub. Date: Apr. 23, 2015

(65) Prior Publication Data
US 2016/0235865 A1  Aug. 18, 2016

Related U.S. Application Data

(60) Provisional application No. 61/890,600, filed on Oct. 14, 2013.

(51) Int. Cl.
*A61K 49/00* (2006.01)
*A61K 41/00* (2006.01)
*C07F 7/18* (2006.01)
*A61K 31/409* (2006.01)
*C07D 487/22* (2006.01)

(52) U.S. Cl.
CPC ........ *A61K 49/0052* (2013.01); *A61K 31/409* (2013.01); *A61K 41/0057* (2013.01); *C07D 487/22* (2013.01); *C07F 7/1804* (2013.01)

(58) Field of Classification Search
CPC ................................ A61K 51/00; A61K 49/00
See application file for complete search history.

(56) References Cited

U.S. PATENT DOCUMENTS

| | | | |
|---|---|---|---|
| 2008/0193381 A1 | 8/2008 | Babich et al. | |
| 2010/0104645 A1 | 4/2010 | Ali et al. | |
| 2010/0324008 A1 | 12/2010 | Low et al. | |
| 2011/0064657 A1* | 3/2011 | Pomper | A61K 31/145 424/1.69 |
| 2012/0009121 A1* | 1/2012 | Pomper | C07D 209/14 424/1.11 |
| 2013/0034494 A1 | 2/2013 | Babich et al. | |

FOREIGN PATENT DOCUMENTS

| | | |
|---|---|---|
| WO | 2009-002529 A2 | 12/2008 |
| WO | 2010-014933 A2 | 2/2010 |
| WO | 2010-108125 A2 | 9/2010 |
| WO | 2013-082338 A1 | 6/2013 |

OTHER PUBLICATIONS

Tiancheng Liu et al. Targeted photodynamic therapy for prostate cancer: Inducing apoptosis via activation of the caspase-8/3-cascade pathway, International J. Oncology, 36, 777-784, 2010.*
Tiancheng Liu et al. Targeted photodynamic therapy for prostate cancer: Including apoptosis via activation of the caspase-8/-3 cascade pathway, International Journal of Oncology, 36, 777-784 (Year: 2010).*
International Search Report and Written Opinion dated Jan. 19, 2015, from related PCT Patent Application No. PCT/US14/060461.
Liu, Tiancheng et al., "Targeted photodynamic therapy for prostate cancer: inducing apoptosis via activation of the caspase-8/-3 cascade pathway," International Journal of Oncology, 2010, vol. 36, pp. 777-784.

* cited by examiner

*Primary Examiner* — Michael G. Hartley
*Assistant Examiner* — Jagadishwar R Samala
(74) *Attorney, Agent, or Firm* — Casimir Jones, S.C.; Jeffrey W. Childers

(57) ABSTRACT

Urea-based photosensitizers, which target prostate-specific membrane antigen (PSMA) for imaging and targeted therapy of PSMA-expressing tumors and cancers are disclosed.

14 Claims, 6 Drawing Sheets

PROSTATE-SPECIFIC MEMBRANE ANTIGEN-TARGETED PHOTOSENSITIZERS FOR PHOTODYNAMIC THERAPY

CROSS-REFERENCE TO RELATED APPLICATIONS

This application is a 35 U.S.C. § 371 National Stage Entry of International Application No. PCT/US14/060461 having an international filing date of Oct 14, 2014, which claims the benefit of U.S. Provisional Application No. 61/890,600, filed Oct 14, 2013, the contents of each of the aforementioned applications are herein incorporated by reference in their entirety.

BACKGROUND

Photodynamic therapy (PDT) is a minimally invasive cancer treatment and has been used in clinic to improve cancer patients' quality of life and survival time. The lack of specific delivery of the photosensitizers, however, is a significant limitation of PDT. Non-targeted, conventional photodynamic therapy cannot deliver the photosensitizers specifically to the tumor and the photosensitizers often circulate in the body long after treatment and cause sensitivity to light for several months.

SUMMARY

In some aspects, the presently disclosed subject matter provides a compound of formula (I):

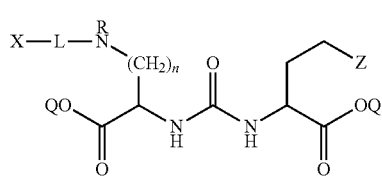

wherein: Z is tetrazole or $CO_2Q$; each Q is independently selected from hydrogen or a protecting group; n is an integer selected from the group consisting of 1, 2, 3, and 4; R is H or $C_1$-$C_4$ alkyl; L is a linker group; and X is H or a photosensitizer moiety; or a pharmaceutically acceptable salt thereof.

In other aspects, the presently disclosed subject matter provides a fluorescence imaging agent comprising a compound of formula (I).

In yet other aspects, the presently disclosed subject matter provides a method for treating a prostate-specific membrane antigen (PSMA)-expressing tumor or cell, the method comprising administering a therapeutically effective amount of compound of formula (I) to a subject in need thereof.

In still yet further aspects, the presently disclosed subject matter provides a method of monitoring a target uptake or a response to therapy for treating a PSMA-expressing tumor or cell, the method comprising administering an effective amount of a compound of formula (I) to a subject in need of treatment thereof, and measuring a fluorescence thereof.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
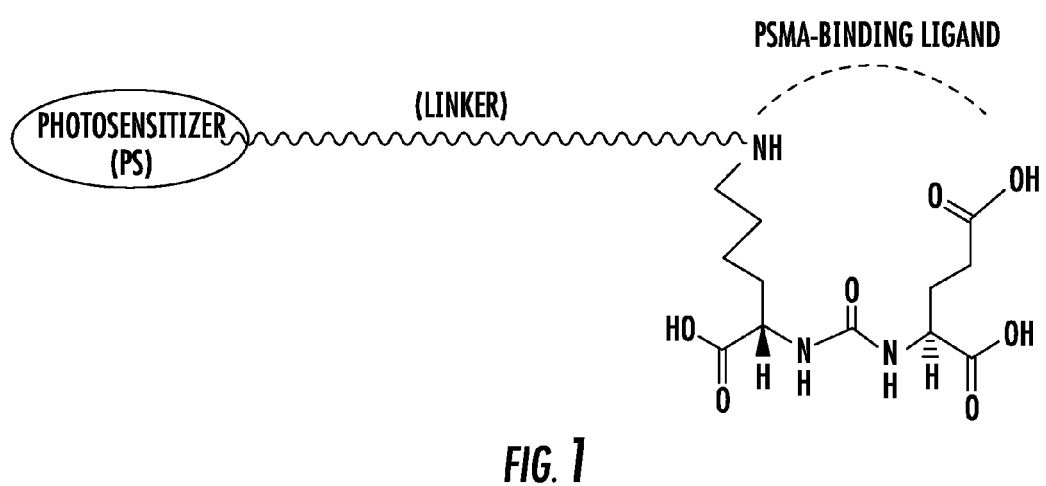
Figure 2:
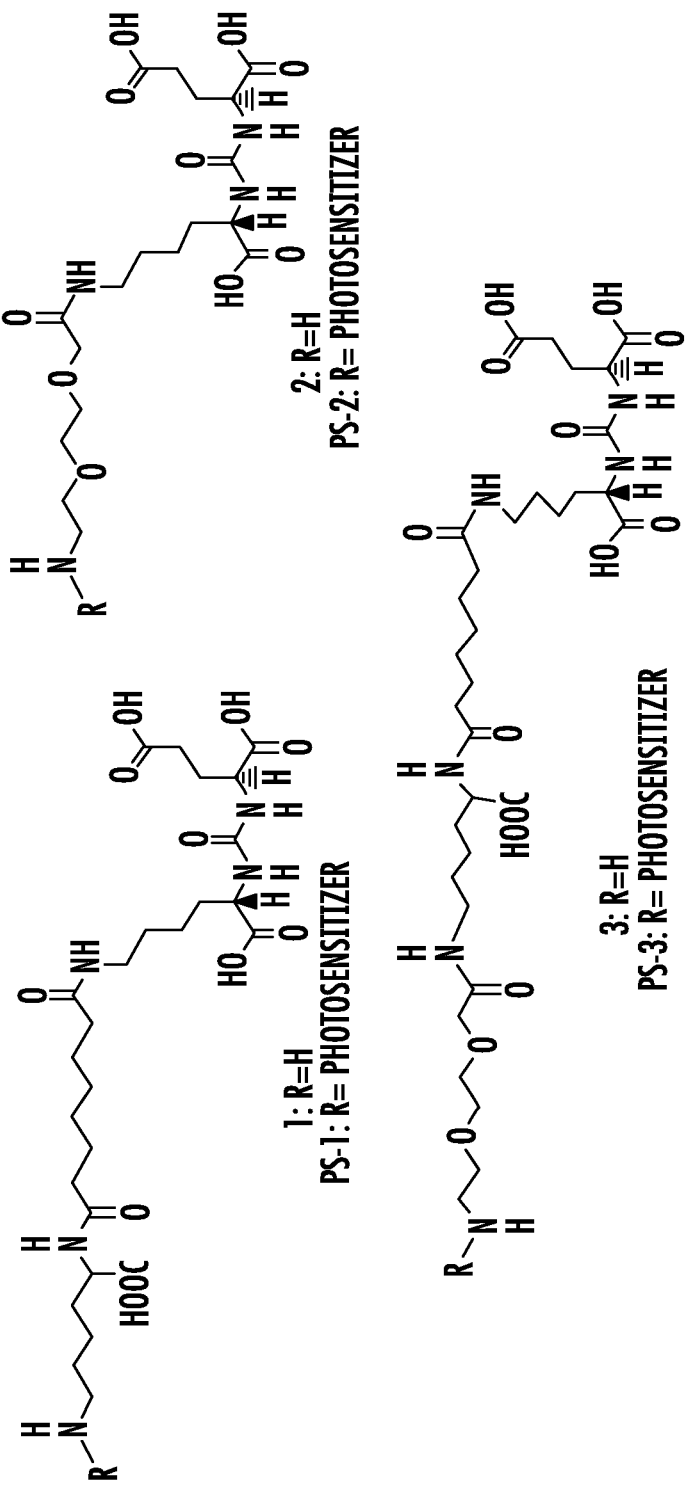
Figure 3:
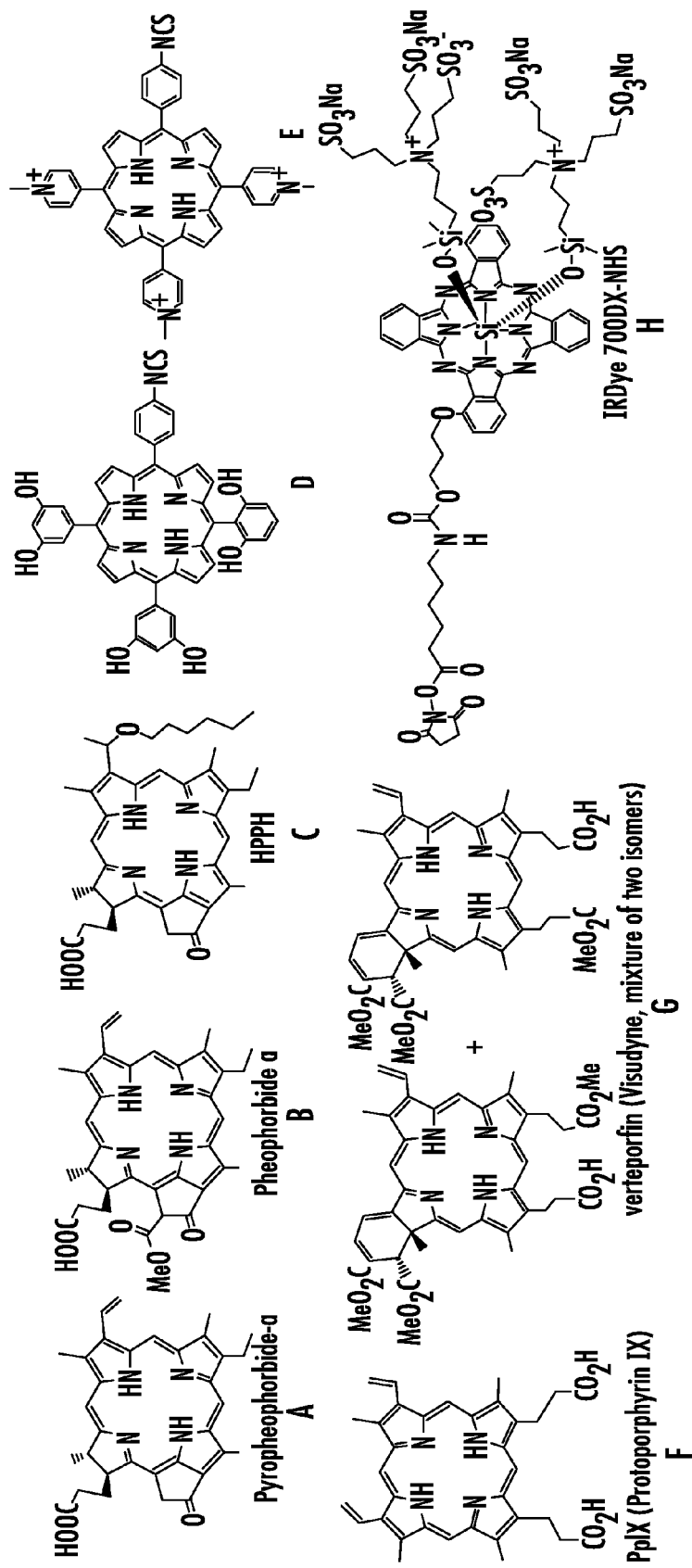
Figure 4:
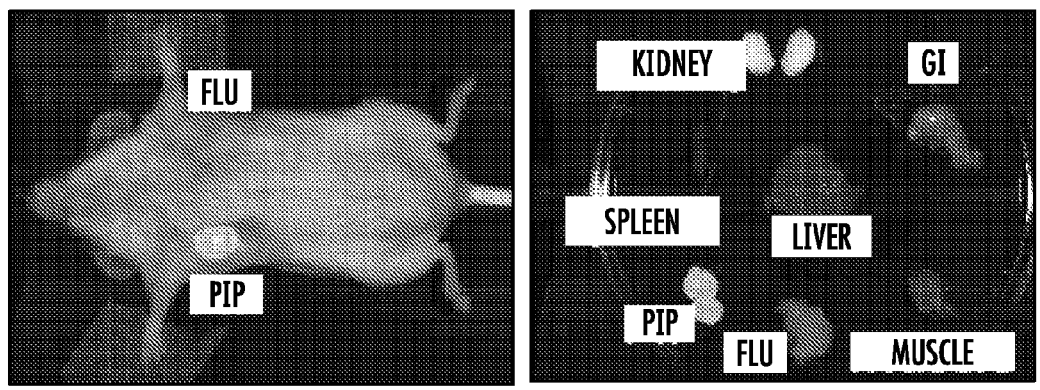
Figure 5:
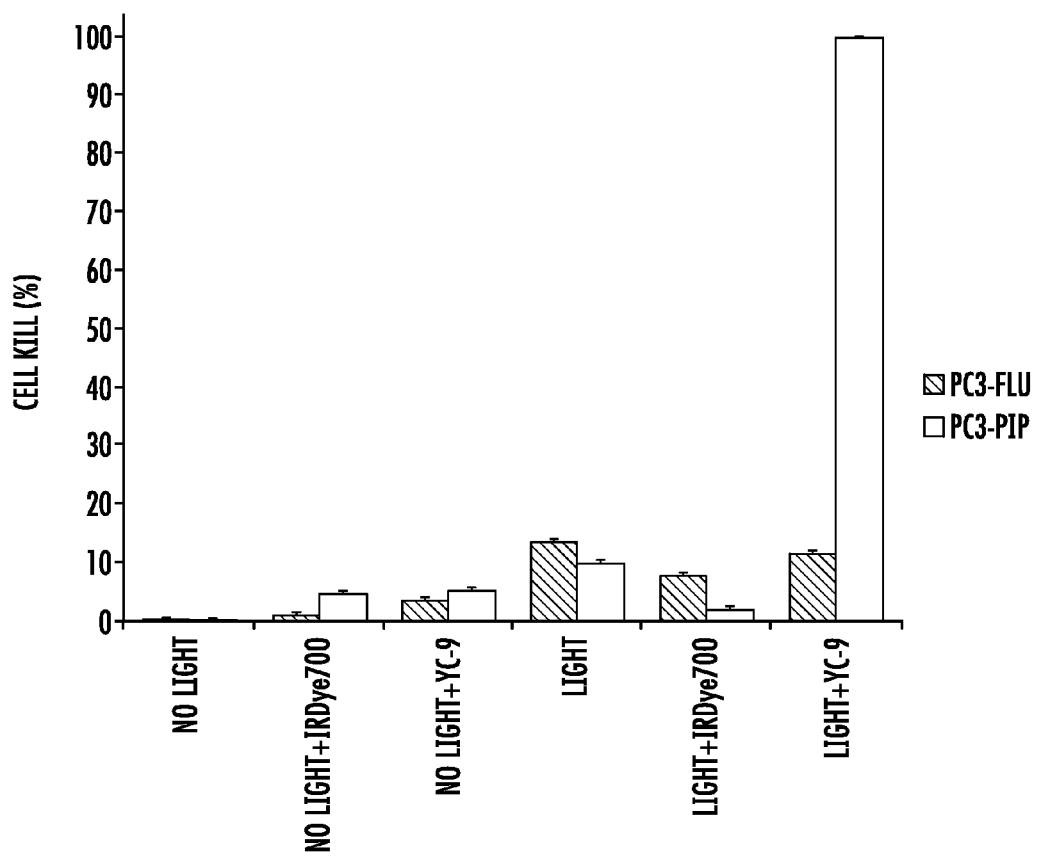
Figure 6:
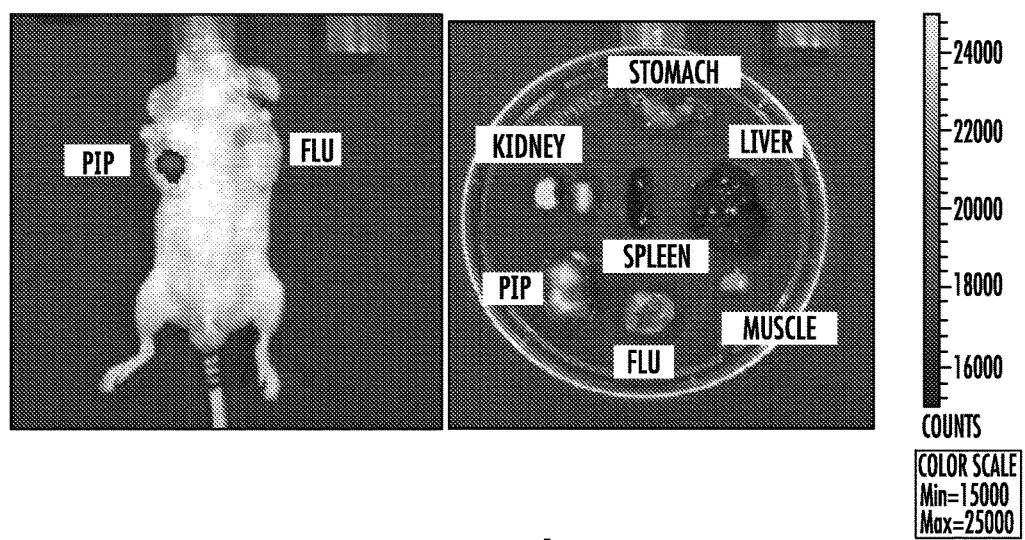

Having thus described the presently disclosed subject matter in general terms, reference will now be made to the accompanying Figures, which are not necessarily drawn to scale, and wherein:

FIG. 1 shows a general schematic of the presently disclosed urea-based photosensitizers;

FIG. 2 shows representative linkers for use with the presently disclosed urea-based photosensitizers;

FIG. 3 shows representative photosensitizer moieties for use with the presently disclosed urea-based photosensitizers;

FIG. 4 is whole body (left) and ex vivo organ (right) imaging of mouse with PSMA+PC3 PIP and PSMA-PC3 flu tumors at 24-h post injection of 10 nmol of YC-9;

FIG. 5 shows YC-9 efficiently and specifically kills PSMA-expressing cells in vitro; and FIG. 6 is whole body (left) and ex vivo organ (right) imaging of mouse with PSMA+PC3 PIP and PSMA-PC3 flu tumors at 24-h post injection of 50 nmol of YC-6.

DETAILED DESCRIPTION

The presently disclosed subject matter now will be described more fully hereinafter with reference to the accompanying Examples and Figures, in which some, but not all embodiments of the presently disclosed subject matter are illustrated.

The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Examples and Figures. Therefore, it is to be understood that the presently disclosed subject matter is not to be limited to the specific embodiments disclosed and that modifications and other embodiments are intended to be included within the scope of the appended claims.

I. Prostate-Specific Membrane Antigen-Targeted Photosensitizers for Photodynamic Therapy The presently disclosed subject matter provides urea-based photosensitizers (FIG. 1), which target prostate-specific membrane antigen (PSMA). PSMA is a type II integral membrane protein that is abundantly expressed in prostate cancer and endothelium of neovasculature in most solid tumors. These characteristics make PSMA an excellent target for imaging and targeted therapy for these cancers.

The presently disclosed PSMA-targeted photosensitizers include three functional parts: (1) a photosensitizer; (2) a PSMA binding ligand; and (3) a linker that tethers the PSMA binding ligand to the photosensitizer.

Lysine-glutamate-urea serves as a tumor-homing molecule that guides the photosensitizer to the PSMA expressing tumor cells. Referring now to FIG. 2, the linker, which is used to improve the pharmacokinetics in vivo, can be, but is not limited to: lysine-suberate (as in compound 1), polyethylene glycol (PEG, as in compound 2), and PEG-lysine-suberate linker (as in compound 3). Further, the photosensitizers moieties can be, but are not limited to, the moieties provided in FIG. 3. Representative PSMA-binding ligands are disclosed in International PCT Patent Application Publication No. WO2010/108125 for "PSMA-Targeting Compounds and Uses Thereof," to Pomper et al., which is incorporated herein by reference in its entirety.

A. Compounds of Formula (I)

In some embodiments, the presently disclosed subject matter provides a compound of formula (I):

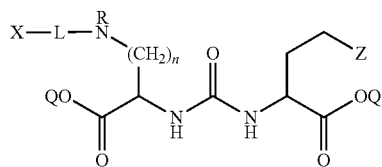

(I)

wherein: Z is tetrazole or $CO_2Q$; each Q is independently selected from hydrogen or a protecting group; n is an integer selected from the group consisting of 1, 2, 3, and 4; R is H or $C_1$-$C_4$ alkyl; L is a linker group; and X is H or a photosensitizer moiety; or a pharmaceutically acceptable salt thereof.

In some embodiments, the linker group has the formula -$L_1$-$L_2$-$L_3$-, wherein each $L_1$, $L_2$, and $L_3$ can be present or absent and can be arranged in any order, and wherein: $L_1$ is —NH—$(CH_2)_m$—[O—$CH_2$—$CH_2$—O]$_p$—$(CH_2)_q$—C(=O)—; $L_2$ is —NH—$(CH_2)_s$—C(COOH)—NH—; and $L_3$ is —(O=)C—$(CH_2)_t$—C(=O)—; wherein m, p, q, s, and t are each integers selected from the group consisting of 1, 2, 3, 4, 5, and 6.

In some embodiments, the compound of formula (I) has the following stereochemistry:

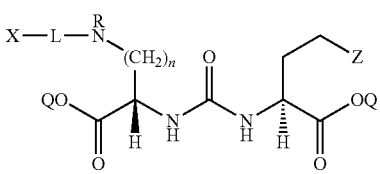

(I')

In particular embodiments, the compound of formula (I) is selected from the group consisting of:

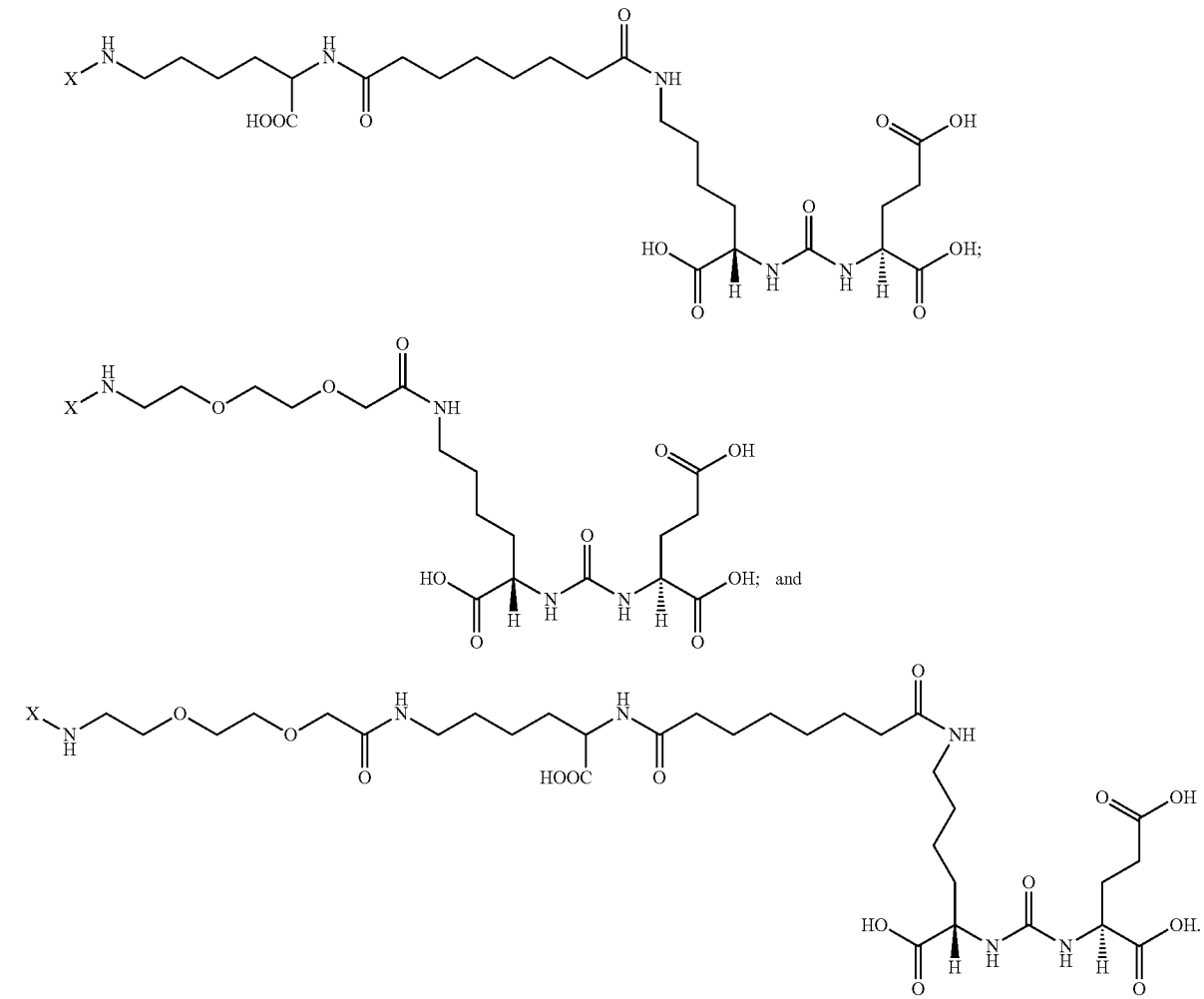

In yet more particular embodiments, the photosensitizer moiety is selected from the group consisting of:
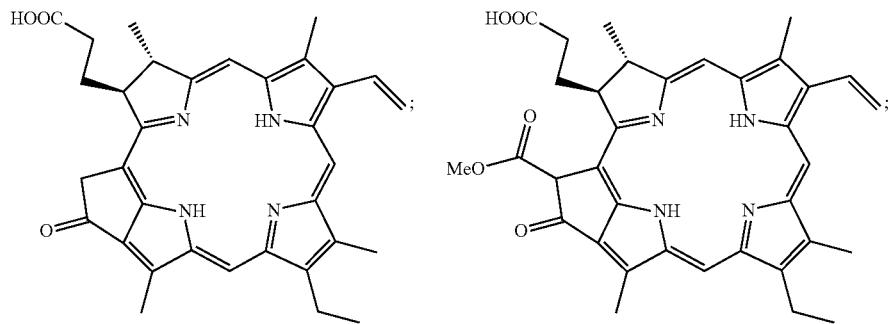
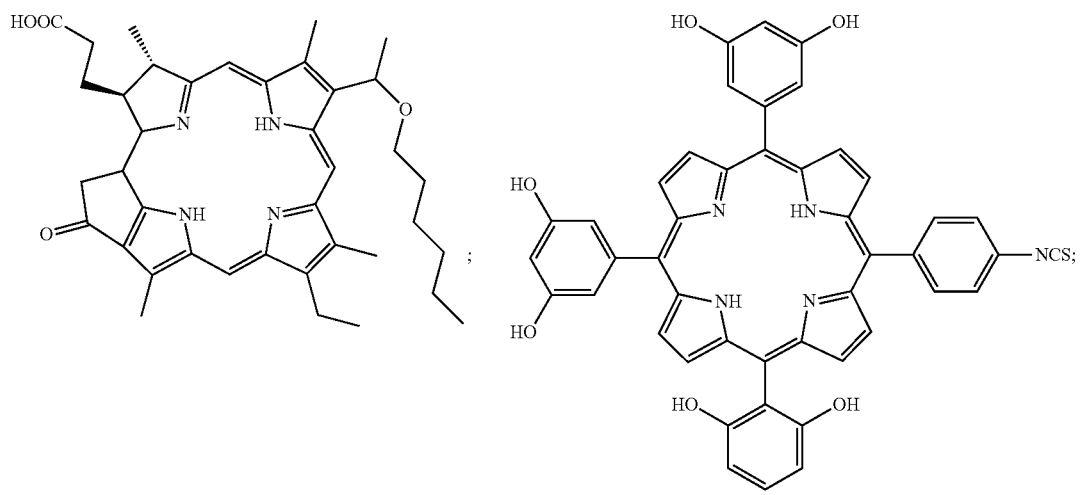
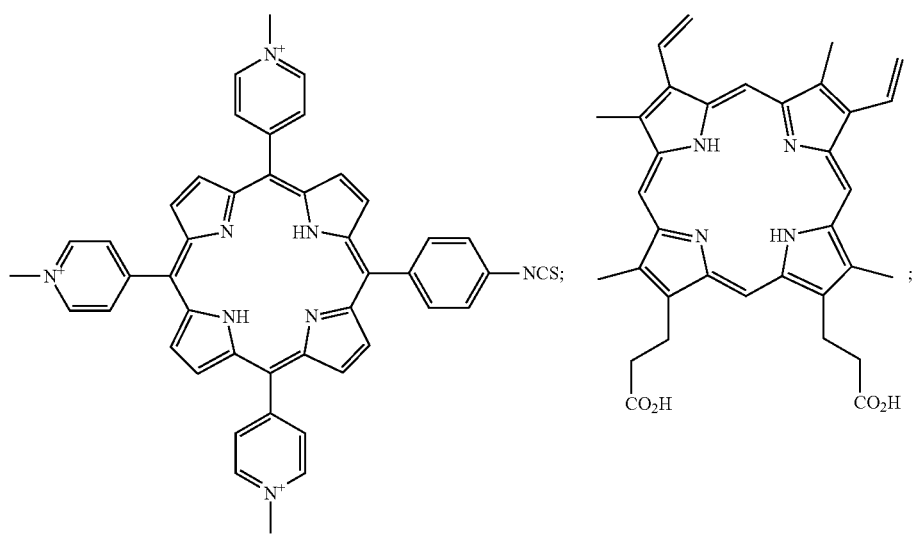

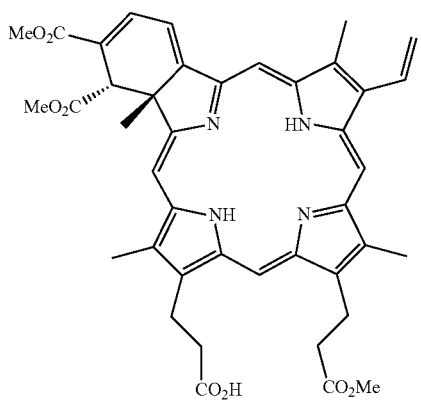

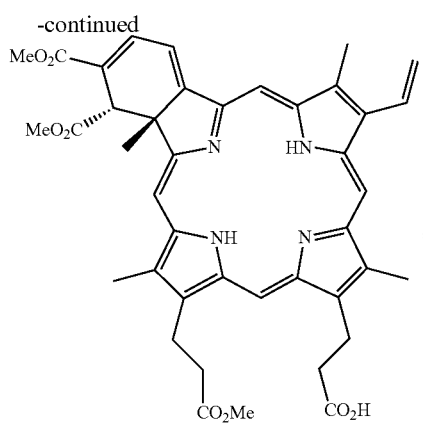

; and

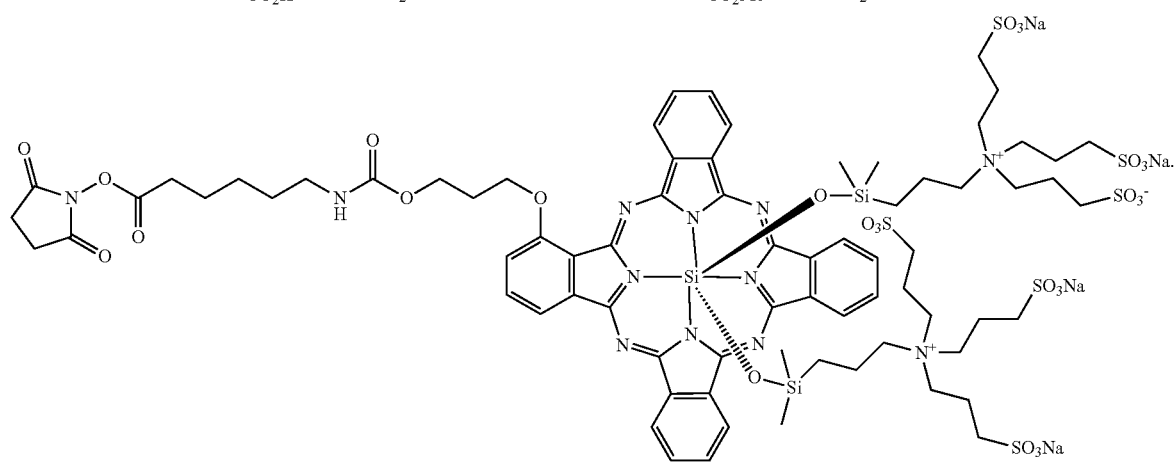

In some embodiments, the presently disclosed subject matter provides a fluorescence imaging agent comprising a compound of formula (I).

i. Chemical Definitions

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like. As used herein, where an internal substituent is flanked by bonds (for example —NRC(O)—) the order of the atoms is fixed, the orientation of the group may not be reversed, and is inserted into a structure in the orientation presented. In other words —NRC(O)— is not the same as —C(O)NR—. As used herein the term C(O) (for example —NRC(O)—) is used to indicate a carbonyl (C=O) group, where the oxygen is bonded to the carbon by a double bond.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

In certain embodiments, alkyl groups are $C_1$-$C_6$ alkyl groups or $C_1$-$C_4$ alkyl groups. The term "$C_1$-$C_6$ alkyl" as used herein means straight-chain, branched, or cyclic $C_1$-$C_6$ hydrocarbons which are completely saturated and hybrids thereof, such as (cycloalkyl)alkyl. Examples of $C_1$-$C_6$ alkyl substituents include methyl (Me), ethyl (Et), propyl (including n-propyl (n-Pr, "Pr), iso-propyl (i-Pr, $^i$Pr), and cyclopropyl (c-Pr, $^c$Pr)), butyl (including n-butyl (n-Bu, "Bu), iso-butyl (i-Bu, $^i$Bu), sec-butyl (s-Bu, sBu), tert-butyl (t-Bu, $^t$Bu), or cyclobutyl (c-Bu, $^c$Bu)), and so forth.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_{2S}-S(O)-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$.

As described above, heteroalkyl groups, as used herein, include those groups that are attached to the remainder of the molecule through a heteroatom, such as $-C(O)R'$, $-C(O)NR'$, $-NR'R''$, $-OR'$, $-SR$, and/or $-SO_2R'$. Where "heteroalkyl" is recited, followed by recitations of specific heteroalkyl groups, such as $-NR'R$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like.

In the term "(cycloalkyl)alkyl", cycloalkyl, and alkyl are as defined above, and the point of attachment is on the alkyl group. This term encompasses, but is not limited to, cyclopropylmethyl, cyclopentylmethyl, and cyclohexylmethyl. The alkyl group may be substituted or unsubstituted.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopropyl, cyclobutyl, cyclopentyl, cyclohexyl, and cycloheptyl.

Multicyclic cycloalkyl rings include adamantyl, octahydronaphthyl, decalin, camphor, camphane, and noradamantyl, and fused ring systems, such as dihydro- and tetrahydronaphthalene, and the like.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$CH_2CH_2CH_2CH_2$—, —$CH_2$CH=CH$CH_2$—, —$CH_2$CsCC$H_2$—, —$CH_2CH_2$CH($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently.

The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, indazolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). The term "haloaryl," however, as used herein, is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

As used herein, the term "alkylaryl" includes alkyl groups, as defined above, substituted by aryl groups, as defined above. The aryl group may be connected at any point on the alkyl group. The term $C_4$-$C_{16}$ alkylaryl includes alkylaryl groups having a total of 4 to 16 carbon atoms, counting the carbon atoms on the alkyl group and aryl group together. Examples of alkylaryl groups include but are not limited to benzyl (phenylmethyl), phenyl ethyl, and naphthylmethyl. The alkylaryl group may be substituted or unsubstituted. Substituents are not counted towards the total number of atoms in the alkylaryl group, so long as the total atoms in the substituent(s) are not larger than the alkylaryl group.

Further, a structure represented generally by the formula:

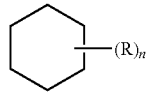

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

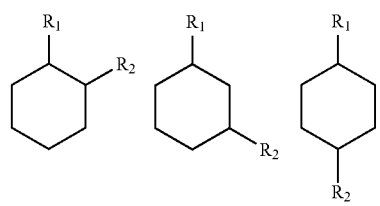

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

A substituent bearing a broken bond, such as the example shown below, means that the substituent is directly bonded to the molecule at the indicated position. No additional methylene ($CH_2$) groups are implied. The symbol ( ⁓ ) denotes the point of attachment of a moiety to the remainder of the molecule.

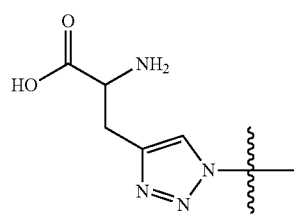 [SMILES: *n1cc(CC(N)C(=O)O)nn1]

Substituents bearing two broken bonds, such as the example shown below, means that the orientation of the atoms is as-indicated, left to right and should be inserted into a molecule in the orientation shown. No additional methylene ($CH_2$) groups are implied unless specifically indicated.

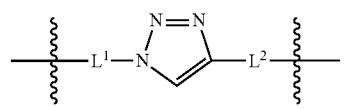

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR' —C(O)NR"R'", —NR"C(O)OR', —NR—C(NR"R") =NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR' —C(O)NR"R'", —NR"C(O)OR', —NR—C (NR'R"R'")=NR"", —NR—C(NR'R") =NR'" —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula —T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula —A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxy substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C═O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, Oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like also can be present in the compounds described herein, and all such stable isomers are contemplated in the presently disclosed subject matter. Cis and trans geometric isomers of the compounds of the presently disclosed subject matter are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated. In certain embodiments, the salt or counter-ion may be pharmaceutically acceptable, for administration to a subject. Pharmaceutically acceptable salts are discussed later.

As used herein, a "protecting group" is a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Specific examples of protecting groups include but are not limited to, benzyl, p-methoxybenzyl (PMB), tertiary butyl ($^1$Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

ii. Pharmaceutical Salts

The compounds of the present disclosure may exist as pharmaceutically acceptable salts. The term "pharmaceutically acceptable salts" is meant to include salts of active compounds which are prepared with relatively nontoxic acids or bases, depending on the particular substituent moieties found on the compounds described herein. Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrates, (e.g. (+)-tartrates, (−)-tartrates or mixtures thereof including racemic mixtures), or teoclate. These salts may be prepared by methods known to those skilled in art. Other pharmaceutically acceptable salts may be found in, for example, Remington: The Science and Practice of Pharmacy (20$^{th}$ ed.) Lippincott, Williams & Wilkins (2000).

Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolyl-sulfonic, citric, tartaric, methanesulfonic, and the like.

Also included are salts of amino acids such as arginate and the like, and salts of organic acids like glucuronic or galactunoric acids and the like, see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

iii. Pharmaceutical Compositions and Kits

The compounds disclosed herein can be formulated into various compositions, for use in diagnostic, imaging or therapeutic treatment methods. The compositions (e.g. pharmaceutical compositions) can be assembled as a kit. Generally, a pharmaceutical composition comprises an effective amount (e.g., a pharmaceutically effective amount, or detectably effective amount) of a compound described above.

A presently disclosed composition can be formulated as a pharmaceutical composition, which comprises a presently disclosed compound and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18$^1$ ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

A pharmaceutical composition or kit of the presently disclosed subject matter can contain other pharmaceuticals, in addition to the compound. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the presently disclosed subject matter.

One skilled in the art will appreciate that a suitable or appropriate formulation can be selected, adapted or developed based upon the particular application at hand. Dosages for presently disclosed compositions can be in unit dosage form. The term "unit dosage form" as used herein refers to physically discrete units suitable as unitary dosages for animal (e.g. human) subjects, each unit containing a predetermined quantity of a presently disclosed agent, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient.

The dose of a presently disclosed composition, administered to an animal, particularly a human, in the context of the presently disclosed subject matter should be sufficient to produce at least a detectable amount of a diagnostic or therapeutic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, and the like. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Other embodiments provide kits including a compound according to the presently disclosed subject matter. In certain embodiments, the kit provides packaged pharmaceutical compositions having a pharmaceutically acceptable carrier and a compound of the presently disclosed subject matter. In some embodiments the packaged pharmaceutical composition will include the reaction precursors necessary to generate the compound of the presently disclosed subject matter upon combination with a radionuclide. Other packaged pharmaceutical compositions provided by the presently disclosed subject matter further comprise indicia comprising at least one of: instructions for preparing compounds according to the presently disclosed subject matter from supplied precursors, instructions for using the composition to image cells or tissues expressing PSMA, or instructions for using the composition to image glutamatergic neurotransmission in a patient suffering from a stress-related disorder, or instructions for using the composition to image prostate cancer.

In certain embodiments, a kit according to the presently disclosed subject matter contains an agent described above in combination with a pharmaceutically acceptable carrier. The agent and carrier may be provided in solution or in lyophilized form. When the agent and carrier of the kit are in lyophilized form, the kit may optionally contain a sterile and physiologically acceptable reconstitution medium such as water, saline, buffered saline, and the like. The kit may provide a compound of the presently disclosed subject matter in solution or in lyophilized form, and these components of the kit of the presently disclosed subject matter may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

Determination and optimization of such stabilizers and stabilization methods are well within the level of skill in the art.

A "pharmaceutically acceptable carrier" refers to a biocompatible solution, having due regard to sterility, p[Eta], isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier also can contain stabilizers, preservatives, antioxidants, or other additives, which are well known to one of skill in the art, or other vehicles as known in the art.

B. Methods of Treatment

The presently disclosed PSMA-targeted PDT agents have been shown to concentrate selectively within PSMA-expressing tumors, therefore they will enhance the specificity and efficiency of PDT. The presently disclosed PSMA-targeted photosensitizers also can serve as fluorescence imaging agents to monitor target uptake and response to therapy.

Embodiments of the presently disclosed subject matter include methods for treating a tumor, the method comprising administering a therapeutically effective amount of one or more presently disclosed compounds to a subject in need of treatment thereof. In some embodiments, the tumor cells express PSMA, such as prostate tumor cells or metastasized prostate tumor cells. In other embodiments, a tumor may be treated by targeting adjacent or nearby cells which express PSMA. For example, vascular cells undergoing angiogenesis associated with a tumor may be targeted. Essentially all solid tumors express PSMA in the neovasculture. Therefore, methods of the presently disclosed subject matter can be used to treat nearly all solid tumors including, but not limited to, lung, renal cell, glioblastoma, pancreas, bladder, sarcoma, melanoma, breast, colon, germ cell, pheochromocytoma, esophageal, and stomach tumors. Also, certain benign lesions and tissues including, but not limited to, endometrium, schwannoma and Barrett's esophagus, can be treated according to the presently disclosed methods.

Accordingly, in some embodiments, the presently disclosed subject matter provides a method for treating a prostate-specific membrane antigen (PSMA)-expressing tumor or cell, the method comprising administering a therapeutically effective amount of compound of formula (I) to a subject in need thereof:

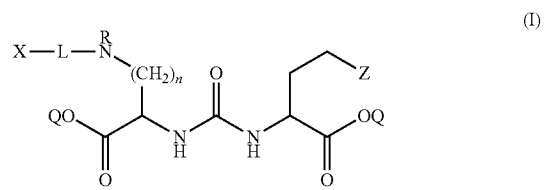

(I)

wherein: Z is tetrazole or $CO_2Q$; each Q is independently selected from hydrogen or a protecting group; n is an integer selected from the group consisting of 1, 2, 3, and 4; R is H or $C_1$-$C_4$ alkyl; L is a linker group; and X is H or a photosensitizer moiety; or a pharmaceutically acceptable salt thereof.

In particular embodiments, the linker group has the formula -$L_1$-$L_2$-$L_3$-, wherein each $L_1$, $L_2$, and $L_3$ can be present or absent and can be arranged in any order, and wherein: $L_1$ is —NH—$(CH_2)_m$—[O—$CH_2$—$CH_2$—O]$_p$—$(CH_2)_q$—C(=O)—; $L_2$ is —NH—$(CH_2)_s$—C(COOH)—NH—; and $L_3$ is —(O=)C—$(CH_2)_t$—C(=O)—; wherein m, p, q, s, and t are each integers selected from the group consisting of 1, 2, 3, 4, 5, and 6.

In some embodiments, the compound of formula (I) has the following stereochemistry:

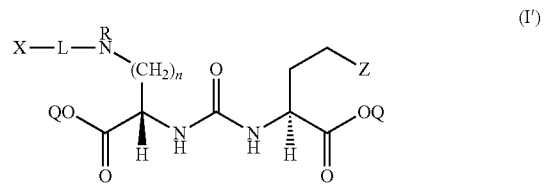

(I')

In more particular embodiments, the compound of formula (I) is selected from the group consisting of:

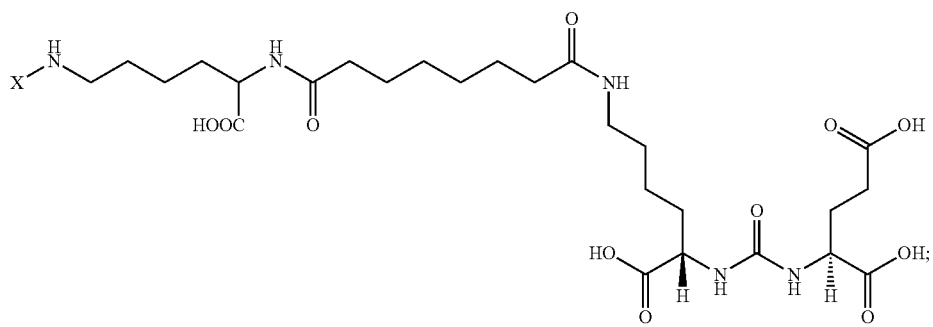

-continued
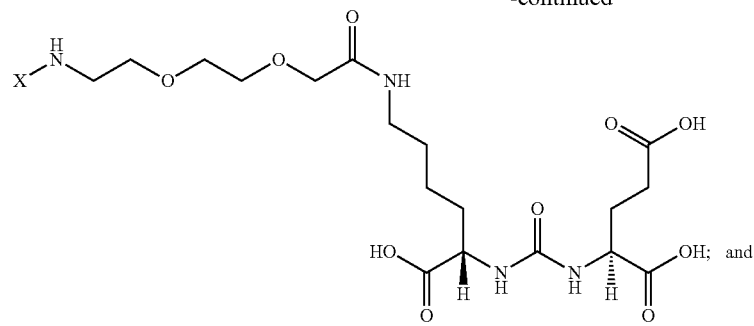
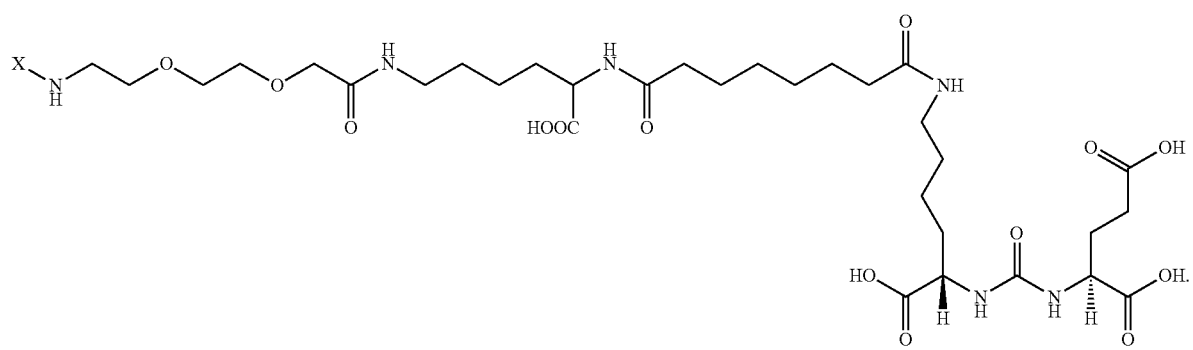
In yet more particular embodiments, the photosensitizer moiety is selected from the group consisting of:
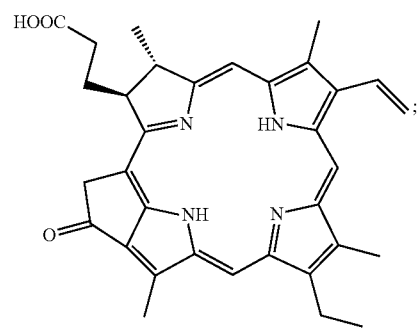
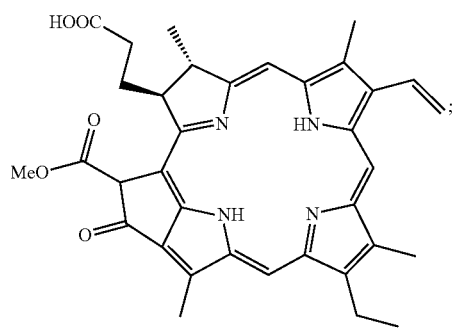
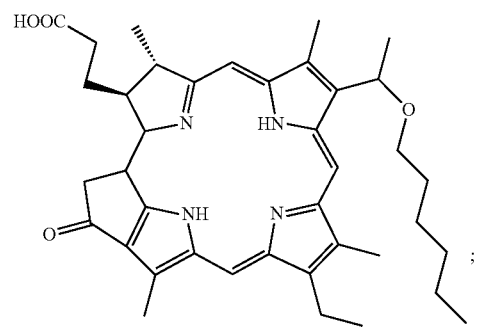
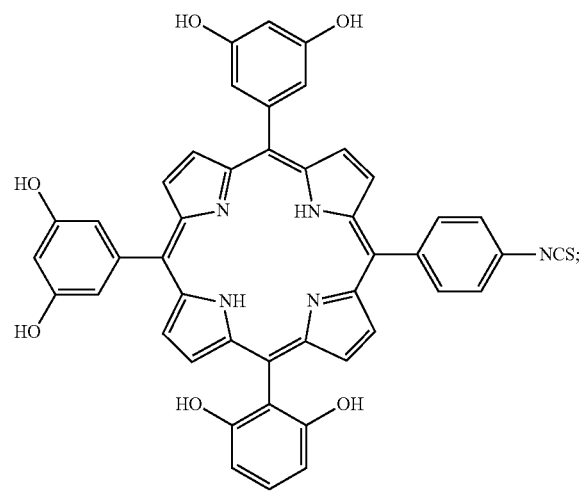

-continued

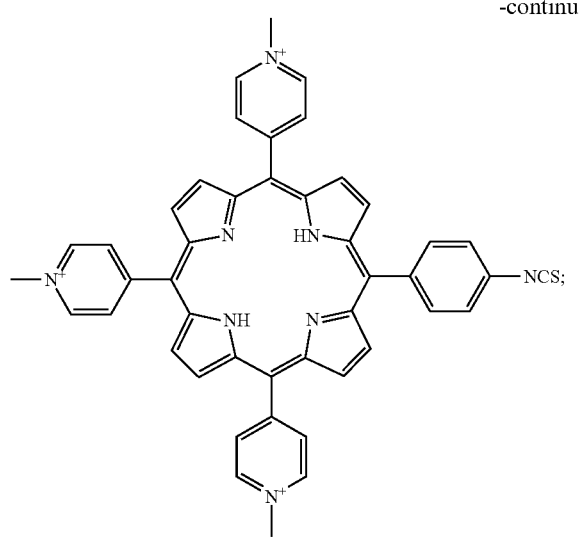

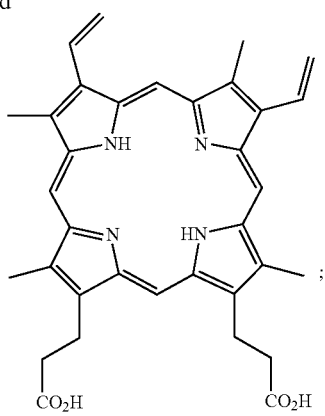

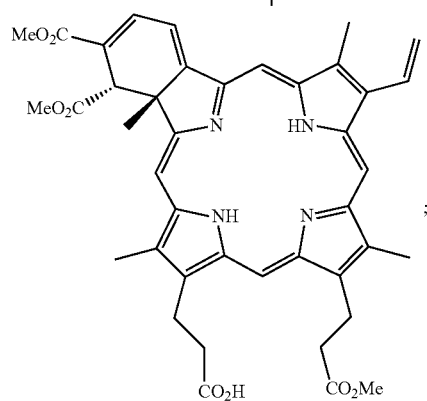

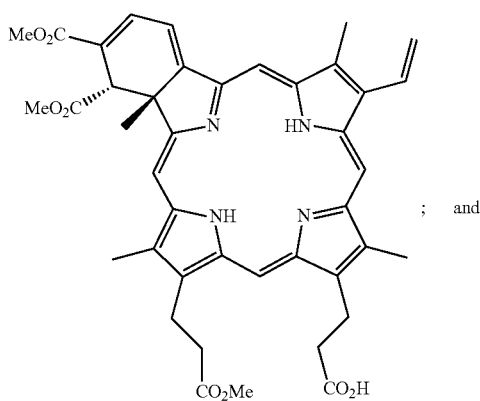

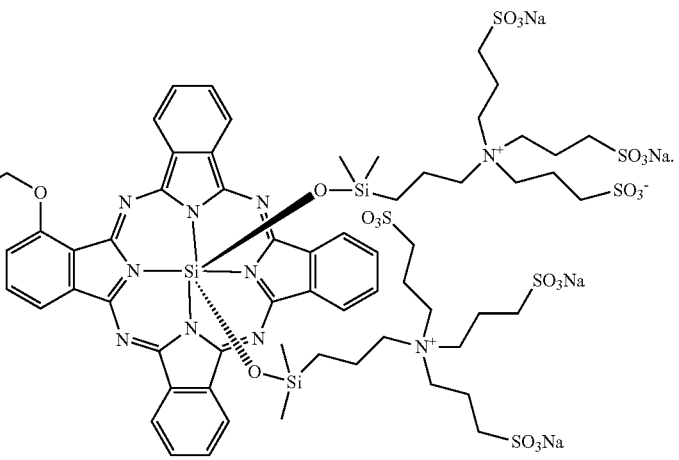

In some embodiments, the PSMA-expressing tumor or cell is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof.

In other embodiments, the PSMA-expressing tumor or cell comprises a benign lesion or tissue.

In yet other embodiments, the benign lesion or tissue is selected from the group consisting of an endometrium, a schwannoma, and Barrett's esophagus.

In further embodiments, the cell comprises a cell adjacent to or nearby a tumor or cell that expresses PSMA. In particular embodiments, the cell comprises a vascular cell undergoing angiogenesis.

C. Method for Monitoring a Target Uptake or a Response to Therapy for Treating a PSMA-Expressing Tumor or Cell In some embodiments, the presently disclosed subject matter provides a method for monitoring a target uptake or a response to therapy for treating a PSMA-expressing tumor or cell, the method comprising administering an effective amount of a compound of formula (I) to a subject in need of treatment thereof, and measuring a fluorescence thereof:

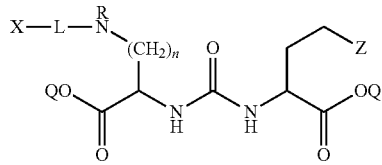
(I)

wherein: Z is tetrazole or $CO_2Q$; each Q is independently selected from hydrogen or a protecting group; n is an integer selected from the group consisting of 1, 2, 3, and 4; R is H or $C_1$-$C_4$ alkyl; L is a linker group; and X is H or a photosensitizer moiety; or a pharmaceutically acceptable salt thereof.

In particular embodiments, the linker group has the formula -$L_1$-$L_2$-$L_3$-, wherein each $L_1$, $L_2$, and $L_3$ can be present or absent and can be arranged in any order, and wherein: $L_1$ is —NH—$(CH_2)_m$—[O—$CH_2$—$CH_2$—O]$_p$—$(CH_2)_q$—C(=O)—; $L_2$ is —NH—$(CH_2)_s$—C(COOH)—NH—; and $L_3$ is —(O=)C—$(CH_2)_t$—C(=O)—; wherein m, p, q, s, and t are each integers selected from the group consisting of 1, 2, 3, 4, 5, and 6.

In some embodiments, the compound of formula (I) has the following stereochemistry:

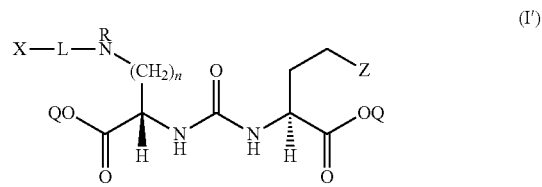
(I')

In more particular embodiments, the compound of formula (I) is selected from the group consisting of:

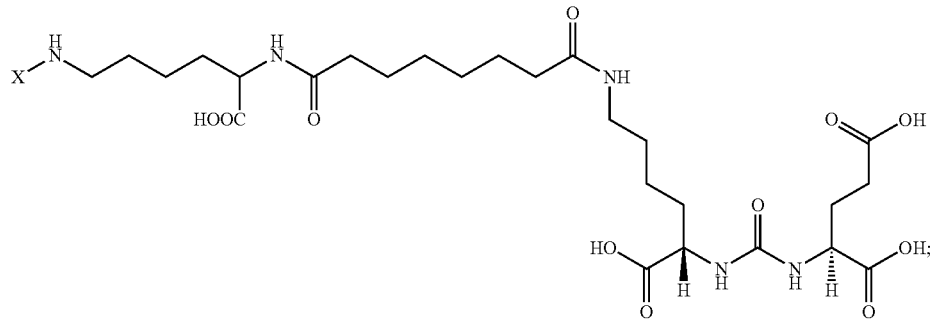

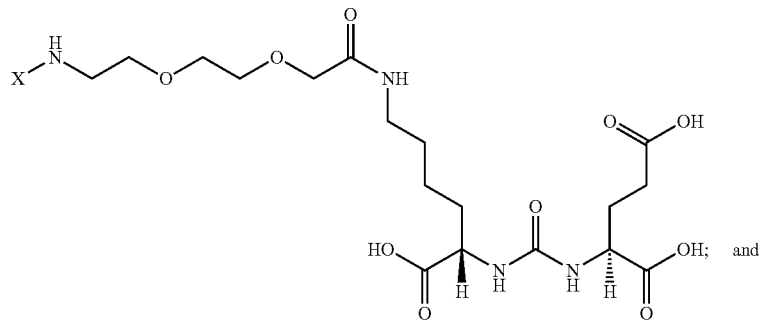

and

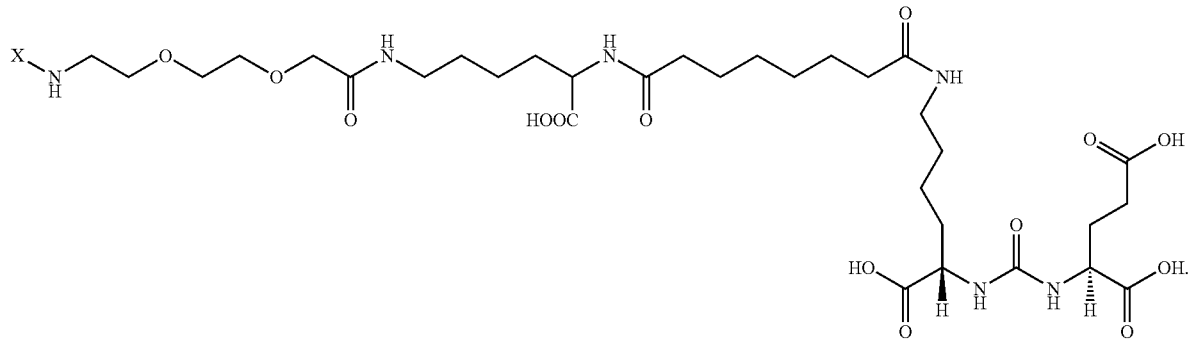

In yet more particular embodiments, the photosensitizer moiety is selected from the group consisting of:
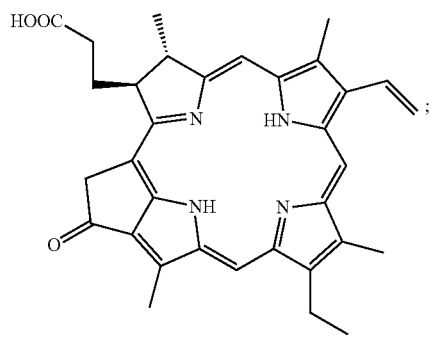
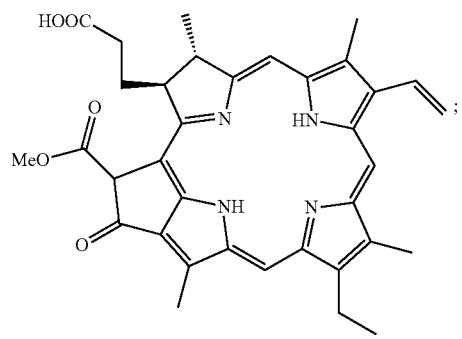
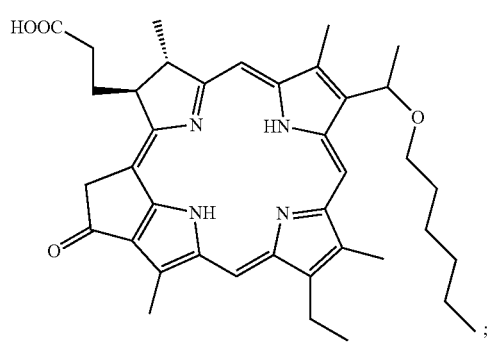
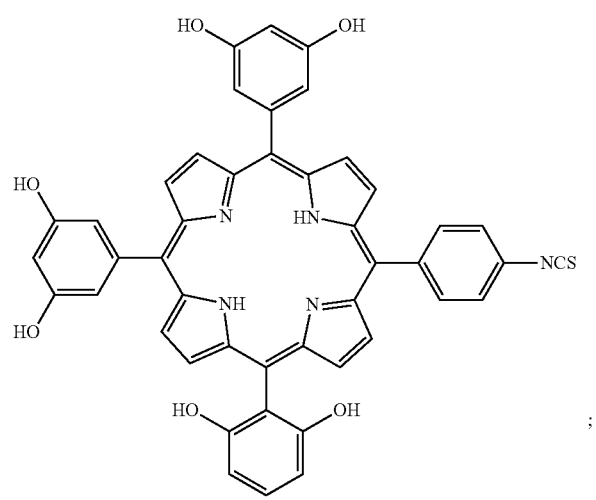
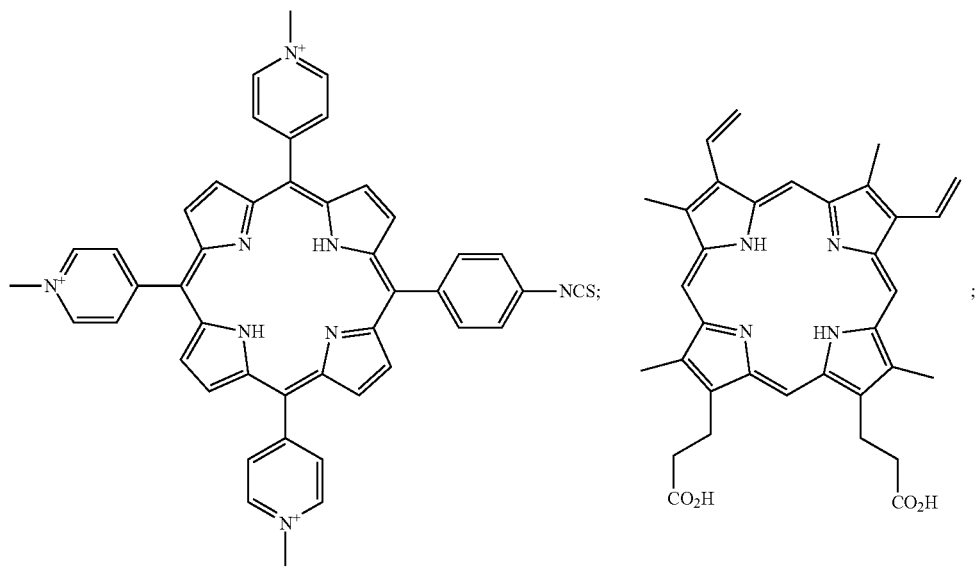

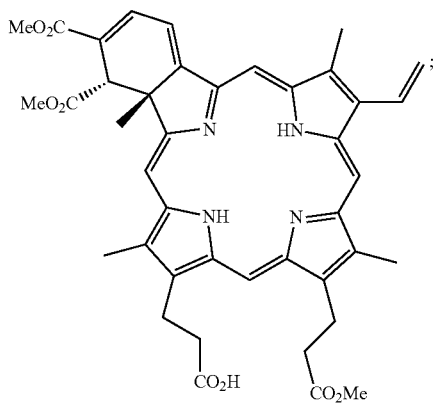

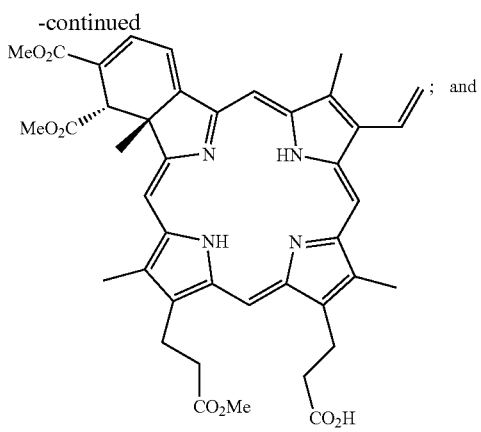

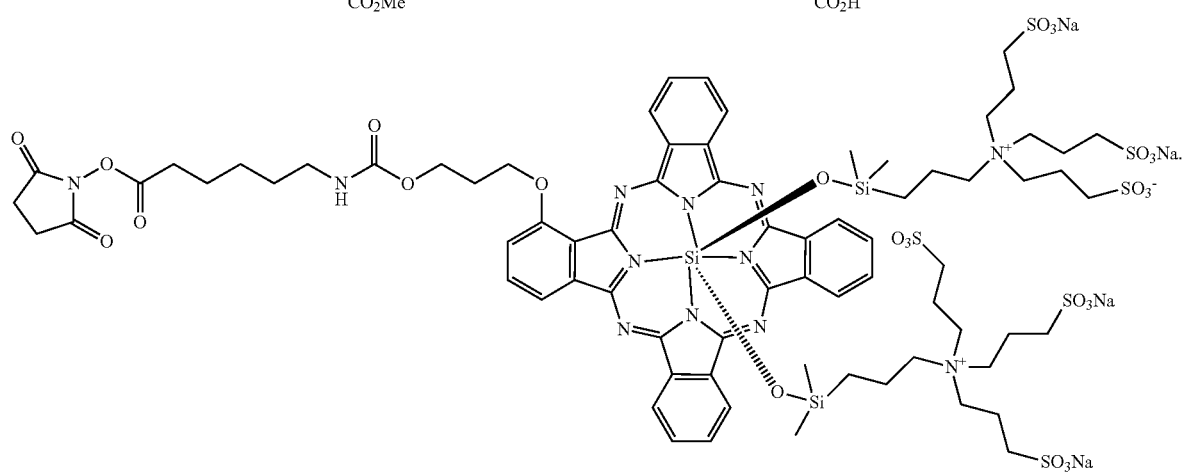

D. General Definitions

Although specific terms are employed herein, they are used in a generic and descriptive sense only and not for purposes of limitation. Particular definitions are provided herein for clarity. Unless otherwise defined, all technical and scientific terms used herein have the same meaning as commonly understood by one of ordinary skill in the art to which this presently described subject matter belongs.

As used herein, the term "agent" refers to a non-peptide, small molecule compound. More generally, the term "therapeutic agent" refers to a non-peptide, small molecule compound that has the potential of affecting the function of an organism. A therapeutic agent may decrease, suppress, attenuate, diminish, arrest, or stabilize the development or progression of disease, disorder, or condition in a host organism or subject.

By "cell substrate" is meant the cellular or acellular material (e.g., extracellular matrix, polypeptides, peptides, or other molecular components) that is in contact with the cell.

By "modifies" is meant alters. An agent that modifies a cell, substrate, or cellular environment produces a biochemical alteration in a component (e.g., polypeptide, nucleotide, or molecular component) of the cell, substrate, or cellular environment.

By "control" is meant a standard or reference condition.

By "disease" is meant any condition or disorder that damages or interferes with the normal function of a cell, tissue, organ, organism, or subject.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

An "effective amount" of an agent refers to the amount of the agent sufficient to elicit a desired biological response or a measurable difference when compared to a control. As will be appreciated by one of ordinary skill in the art, the absolute amount of a particular agent that is effective for treating a disease, disorder, condition, or injury can vary depending on such factors as the agent to be delivered, the manner of administration, the age, body weight, and general health of the subject, the desired biological endpoint, the desired therapeutic effect, and the like. Ultimately, an attending clinician will decide the appropriate amount and dosage regimen. For example, an "effective amount" of an agent can be an amount sufficient to produce a measurable image when the compound is used for imaging, or an amount sufficient to ameliorate the symptoms of a disease when the compound is used for therapy. One of ordinary skill in the art will further understand that an effective amount of an agent can be administered in a single dose, or can be achieved by administration of multiple doses.

As used herein, the terms "treat," treating," "treatment," and the like, are used interchangeably and are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy, and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

Further, as used herein, the term "inhibit" or "inhibits" means to decrease, suppress, attenuate, diminish, arrest, or stabilize the development or progression of a disease, disorder, or condition, or the activity of a biological pathway, e.g., by at least 10%, 20%, 30%, 40%, 50%, 60%, 70%, 80%, 90%, 95%, 98%, 99%, or even 100% compared to an untreated control subject, cell, or biological pathway. By the term "decrease" is meant to inhibit, suppress, attenuate, diminish, arrest, or stabilize a symptom of a disease, disorder, or condition. It will be appreciated that, although not precluded, treating a disease, disorder or condition does not require that the disease, disorder, condition or symptoms associated therewith be completely eliminated.

The term "administering" as used herein refers to contacting a subject with a presently disclosed agent.

By "therapeutic delivery device" is meant any device that provides for the release of a therapeutic agent. Exemplary therapeutic delivery devices include tablets and pills, described below, as well as syringes, osmotic pumps, indwelling catheters, delayed-release and sustained-release biomaterials.

In certain embodiments, presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising the presently disclosed compounds. Alternatively, these agents may be part of a single dosage form, mixed together with one or more presently disclosed compounds in a single composition.

By "in combination with" is meant the administration of one or more presently disclosed compounds with one or more therapeutic agents either simultaneously, sequentially, or a combination thereof. Therefore, a cell or a subject can receive one or more presently disclosed compounds and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the one or more presently disclosed compounds and one or more therapeutic agents are administered simultaneously, they can be administered to the cell or administered to the subject as separate pharmaceutical compositions, each comprising either one or more presently disclosed compounds or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Synthesis of YC-9

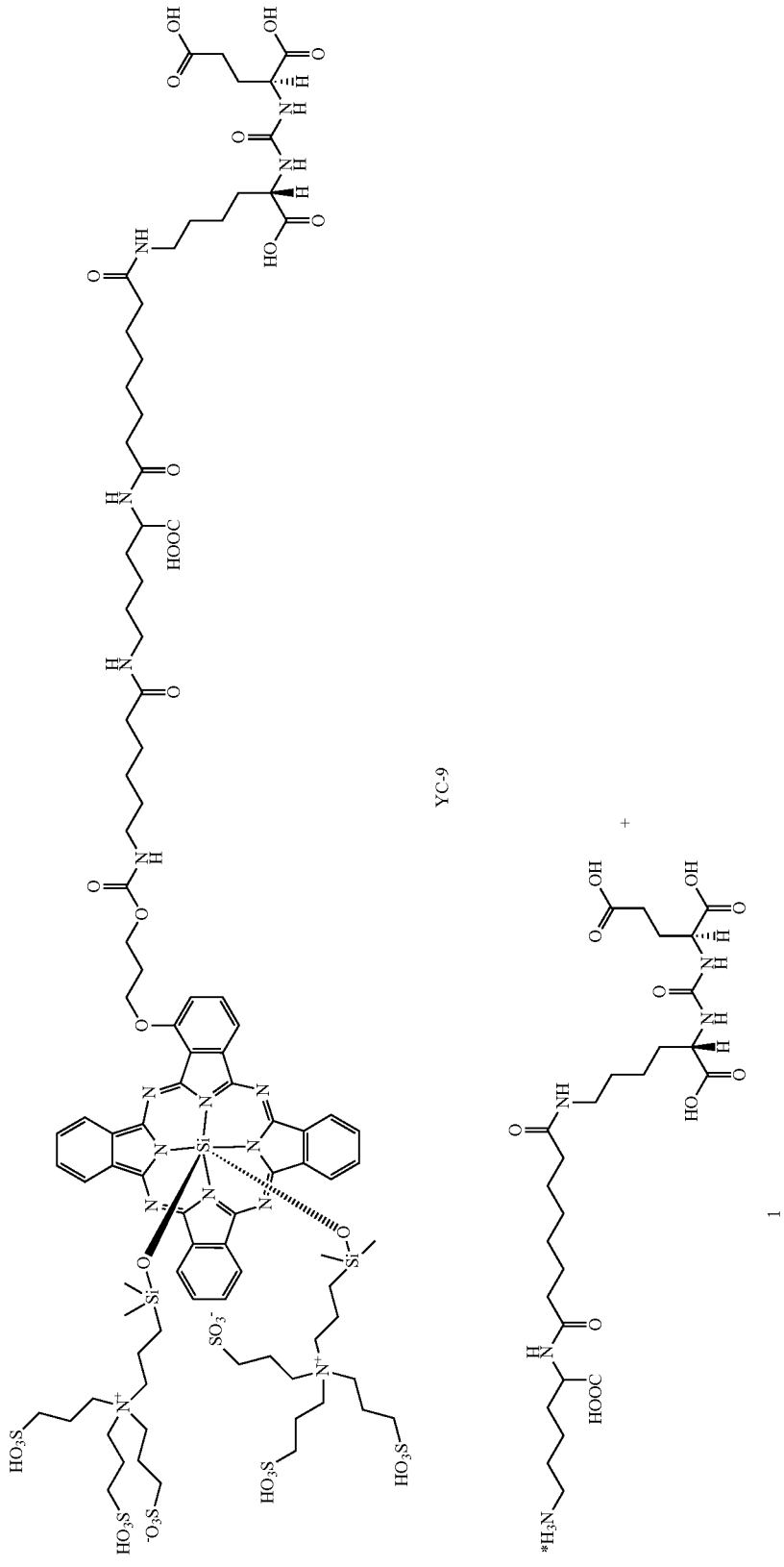
YC-9

-continued
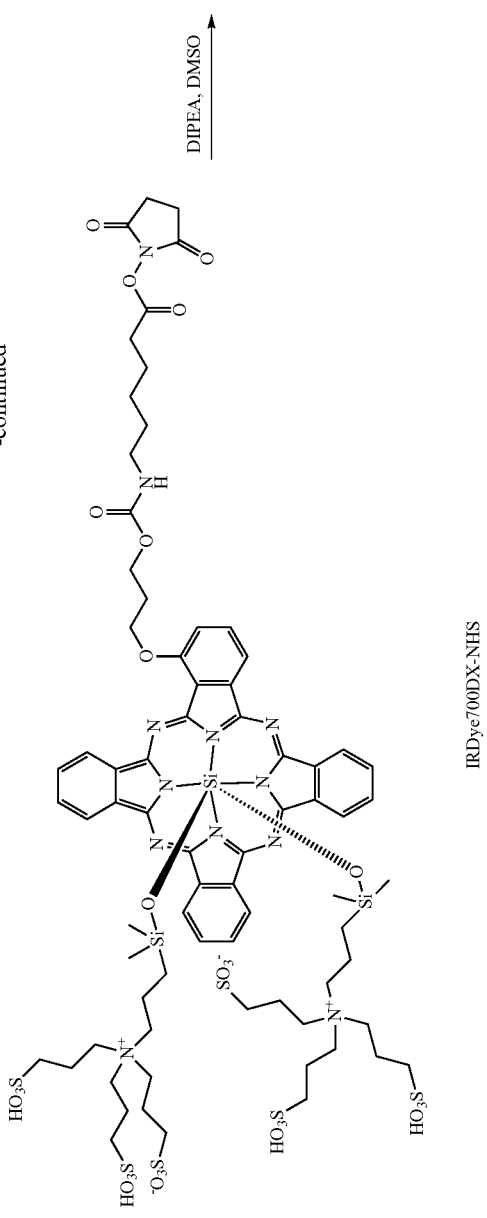
IRDye700DX-NHS
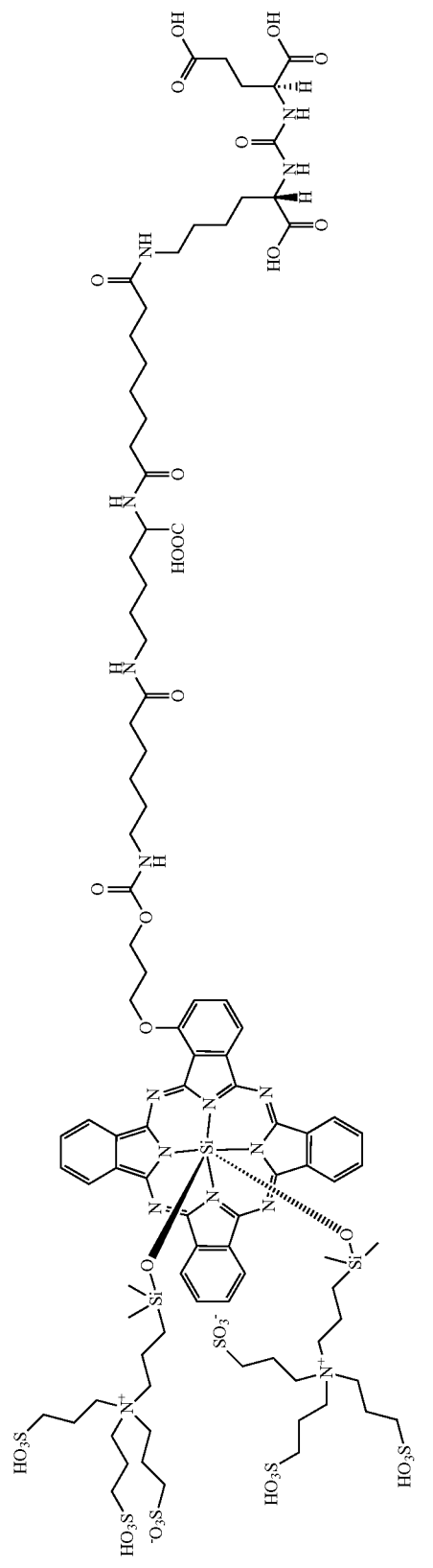
YC-9

To a solution of 1 (0.5 mg, 0.70 µmol) in DMSO (0.1 mL) was added N,N-diisopropylethylamine (0.005 mL, 28.8 µmol), followed by IRDye700DX-NHS (0.5 mg, 0.26 µmol). After 1 h at room temperature, the reaction mixture was purified by HPLC (column, Econosphere C18 5 µm, 150×4.6 mm; retention time, 22 min; mobile phase, A=10 mM triethylammonium acetate (pH 7.0), B=MeOH; gradient, 0 mins=5% B, 5 mins=5% B, 45 mins=100% B; flow rate, 1 mL/min) to afford 0.4 mg (67%) of YC-9. ESI-Mass calcd for $C_{96}H_{138}N_{16}O_{35}S_6Si_3$ $[M-2]^{2-}$, 1175.9, found 1175.3.

PSMA Binding Affinity of YC-9:

The PSMA binding affinity of YC-9 was determined by using a fluorescence-based PSMA binding assay and the $K_i$ value was found to be 0.2 nM.

In Vivo Imaging of YC-9:

In vivo imaging was done using the Pearl Impulse Imager with excitation wavelength of 685 nm and emission wavelength of 700 nm, as well as a white-light overlay. For in vivo study, mouse with PSMA expressing (PC3-PIP) tumor and PSMA non-expressing (PC3-flu) tumor was injected intravenously with 10 nmol of YC-9 images were acquired at 1 h, 6 h and 24 h time points. Following the 24 h image, mouse was sacrificed by cervical dislocation and tumor, muscle, liver, spleen, kidneys and intestine were collected and assembled on a petri dish for image acquisition.

As shown in FIG. 4, the in vivo imaging study of YC-9 showed it concentrated selectively within the PSMA expressing tumor.

In Vitro Photodynamic Therapy:

PSMA expressing (PC3-PIP) and non-expressing (PC3-flu) cells were incubated with no dye, IRDye700DX (100 nM), and YC-9 (100 nM) for 1 hr at 37° C. After washing twice with the media, cells were either irradiated with light (2 J/cm$^2$, 690 nm) or non-irradiated. Cell kill was measured by XTT assay 24 hr post irradiation. Error bar represents standard deviation (n=4). As shown in FIG. 5, YC-9 efficiently and specifically kills PSMA-expressing cells in vitro.

Example 2

Synthesis of YC-6

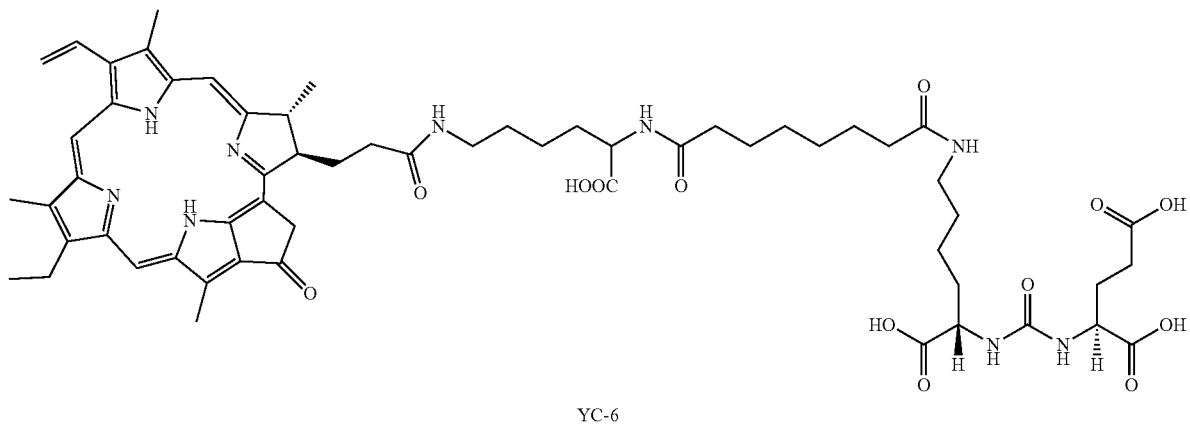 [SMILES: C=Cc1c(C)c2cc3nc(c4c5[nH]c(cc6nc(cc1[nH]2)C(C)=C6CC)c(C)c5C(=O)C4)[C@H](CCC(=O)NCCCCC(NC(=O)CCCCCCC(=O)NCCCC[C@H](NC(=O)N[C@@H](CCC(=O)O)C(=O)O)C(=O)O)C(=O)O)[C@H]3C ; "YC-6"]

YC-6

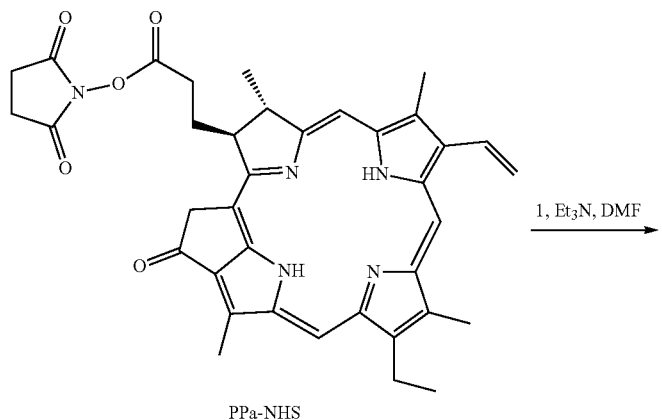

PPa-NHS

1, Et$_3$N, DMF

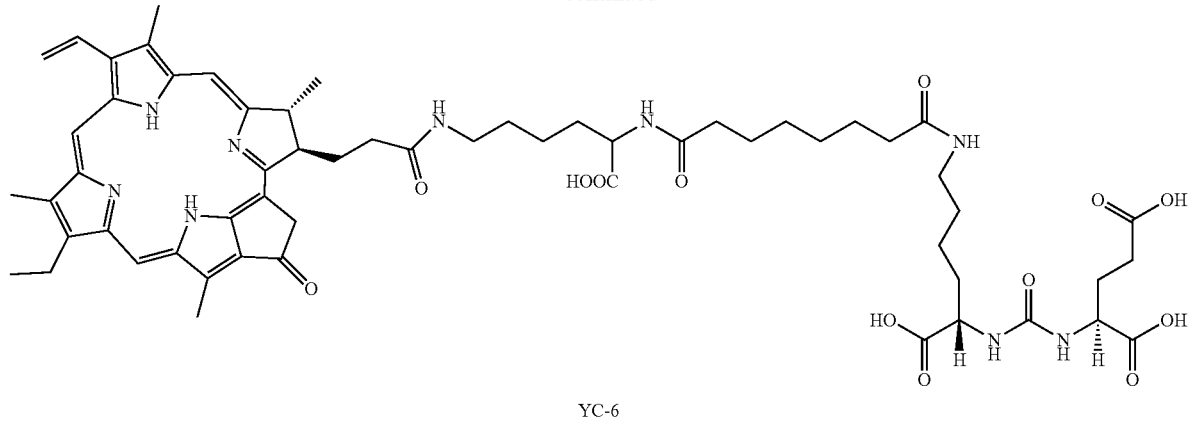

YC-6

PPa—NHS was synthesized according to literature method (*J. Am. Chem. Soc.*, 2005, 127, 8376-8385). To a solution of 1 (1 mg, 1.4 µmol) in DMF (0.1 mL) was added triethylamine (0.005 mL, 35.9 µmol), followed by PPa—NHS (1 mg, 1.6 µmol). After 2 h at room temperature the reaction mixture was purified by HPLC (column, Econosphere C18 5µ, 150×4.6 mm; retention time, 30 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 1.3 mg (83%) of YC-6. ESI-Mass calcd for $C_{59}H_{77}N_9O_{13}$ $[M]^+$, 1119.6. found 1120.0.

PSMA Binding Affinity of YC-6:

The PSMA binding affinity of YC-6 was determined by using a fluorescence-based PSMA binding assay and the $K_i$ value was found to be 1.2 nM.

In Vivo Imaging of YC-6:

Imaging studies with YC-6 were undertaken on the Xenogen IVIS 200 system. FIG. 6 shows the whole body (left) and ex vivo organ (right) imaging of mouse with PSMA+ PC3 PIP and PSMA-PC3 flu tumors at 24 h post injection of 50 nmol of YC-6.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

International PCT Patent Application Publication No. WO/2013/082338 for HOMOMULTIVALENT AND HETEROMULTIVALENT INHIBITORS OF PROSTATE SPECIFIC MEMBRANE ANTIGEN (PMSA) AND USES THEREOF, to Pomper et al., published Jun. 6, 2013;

International PCT Patent Application Publication No. WO/2009/002529 for LABELED INHIBITORS OF PROSTATE SPECIFIC MEMBRANE ANTIGEN (PSMA), BIOLOGICAL EVALUATION, AND USE AS IMAGING AGENTS, to Pomper et al., published Dec. 31, 2008.

International PCT Patent Application Publication No. WO/2010/108125 for PSMA-TARGETING COMPOUNDS AND USES THEREOF, to Pomper et al., published Sep. 23, 2010.

International PCT Patent Application Publication No. WO/2010/014933 for PSMA-BINDING AGENTS AND USES THEREOF, to Pomper et al., published Feb. 4, 2010.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

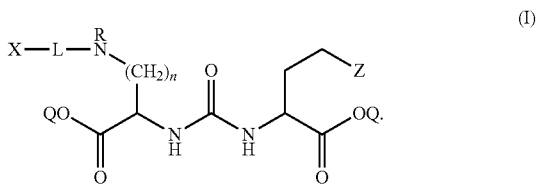

wherein:

Z is tetrazole or $CO_2Q$;

each Q is independently selected from hydrogen or a protecting group;

n is an integer selected from the group consisting of 1, 2, 3, and 4;

R is H or $C_1$-$C_4$ alkyl;

L is a linker group;

and X is a photosensitizer moiety; or a pharmaceutically acceptable salt thereof wherein the photosensitizer moiety is selected from the group consisting of:

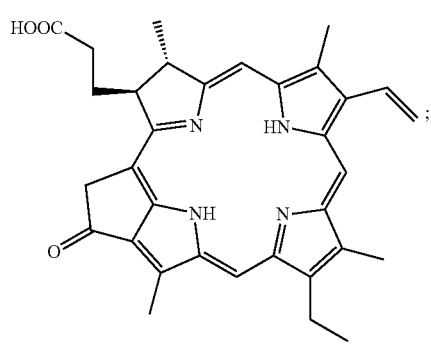
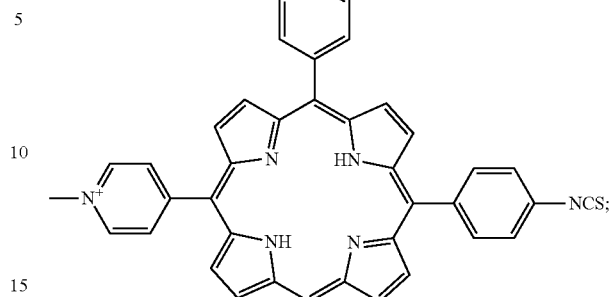
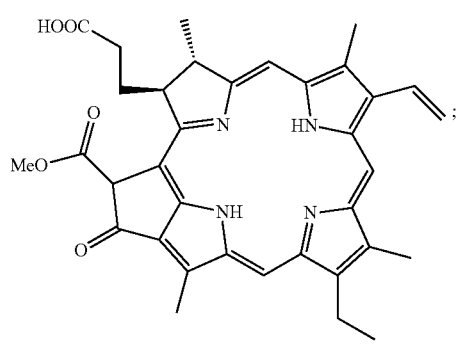
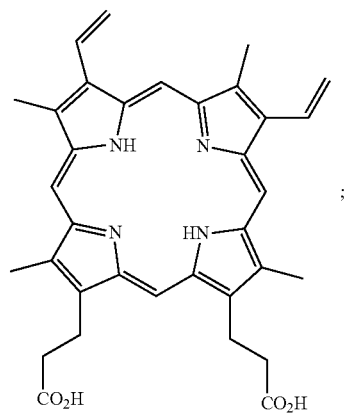
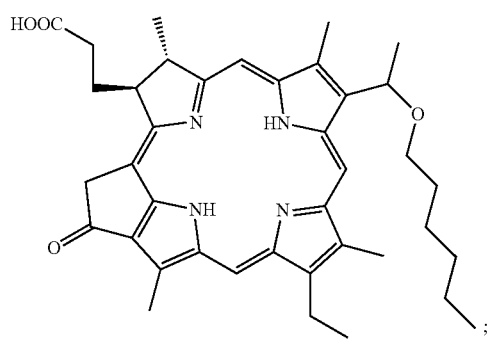
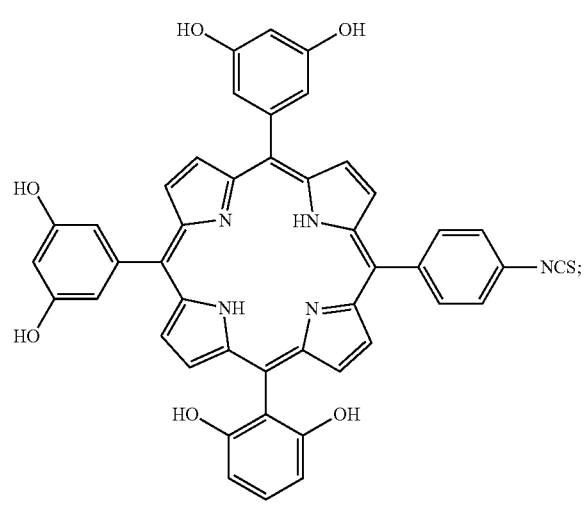
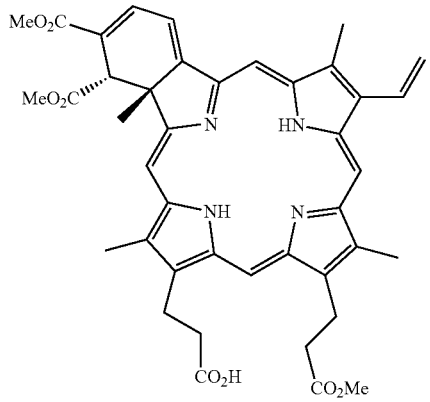

-continued
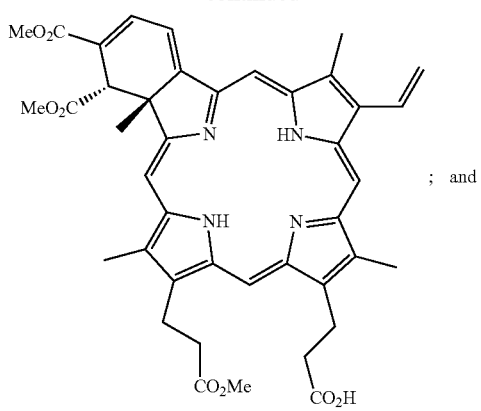
; and
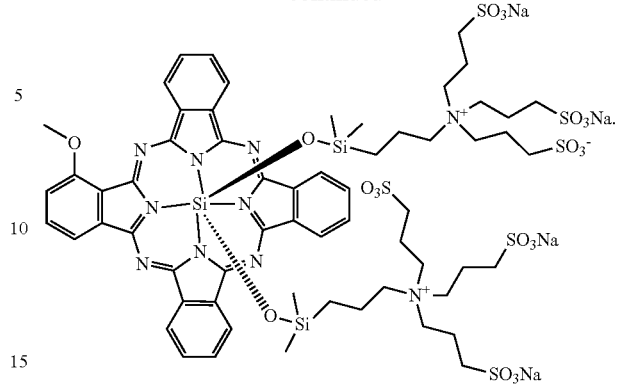
2. The compound of claim 1, wherein the compound has the following stereochemistry:
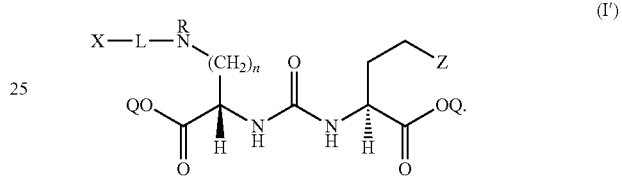
(I')
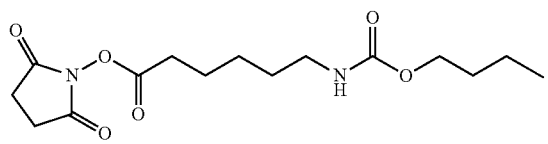
3. The compound of claim 1, wherein the compound of formula (I) is selected from the group consisting of:
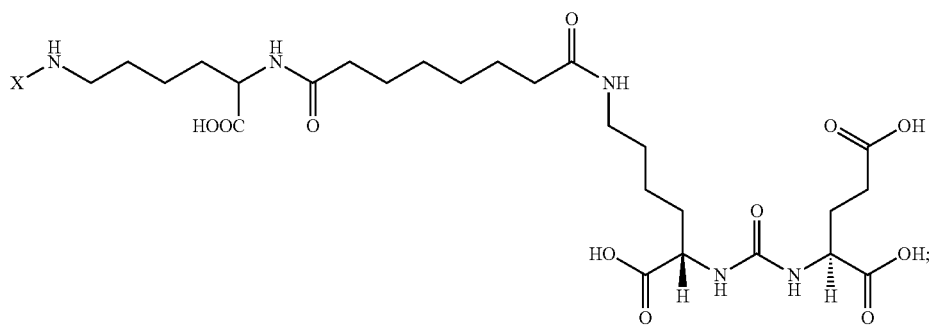
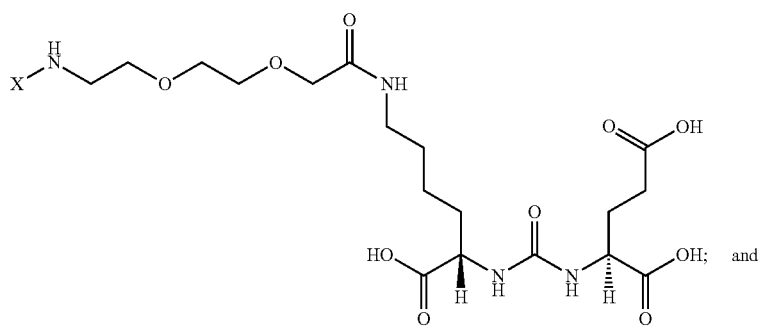
and

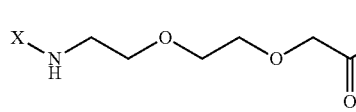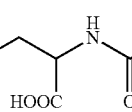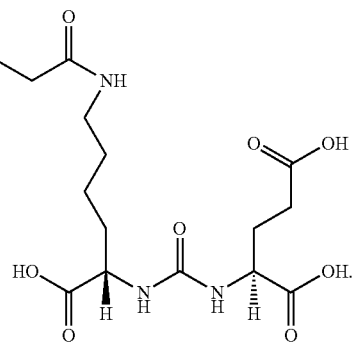

4. A fluorescence imaging agent comprising a compound of claim 1.

5. A method for treating a prostate-specific membrane antigen (PSMA)-expressing tumor or cell, the method comprising administering a therapeutically effective amount of compound of claim 1 to a subject in need thereof:

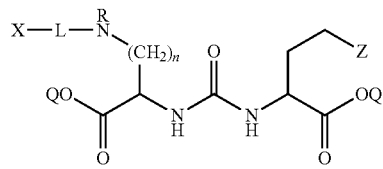 (I)

wherein:
Z is tetrazole or $CO_2Q$;
each Q is independently selected from hydrogen or a protecting group;
n is an integer selected from the group consisting of 1, 2, 3, and 4;
R is H or $C_1$-$C_4$ alkyl;
L is a linker group;
and X is a photosensitizer moiety; or a pharmaceutically acceptable salt thereof.

6. The method of claim 5, wherein the compound of formula (I) has the following stereochemistry:

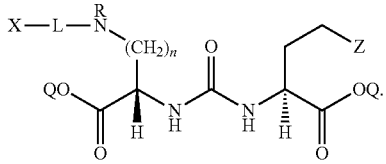 (I')

7. The method of claim 5, wherein the compound of formula (I) is selected from the group consisting of:

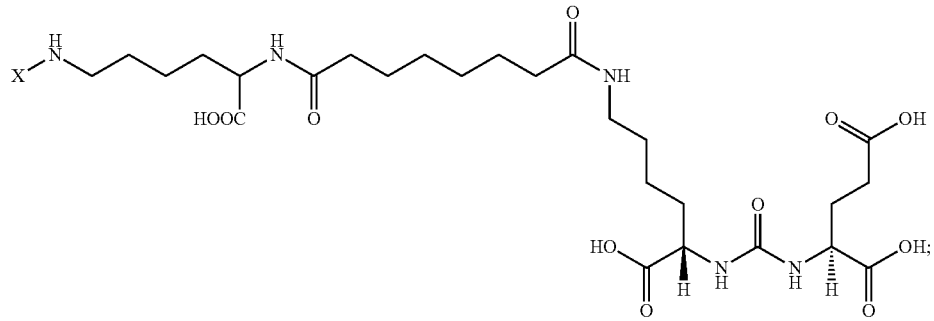

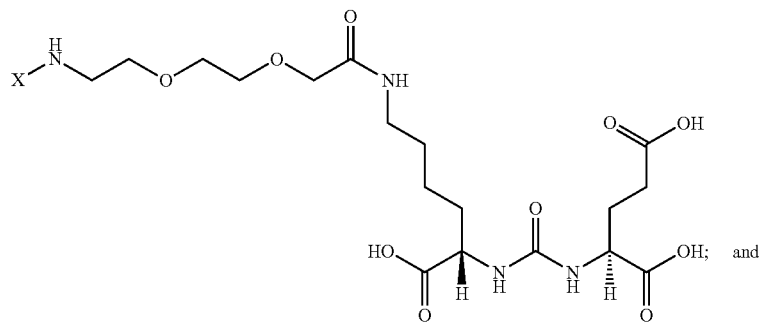 and

-continued

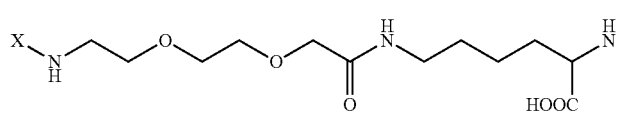
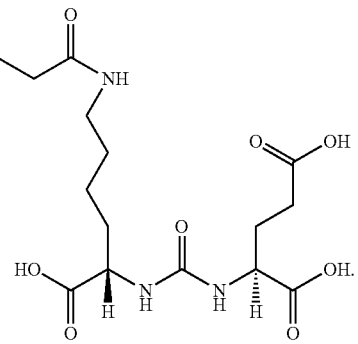

8. The method of claim 5, wherein the PSMA-expressing tumor or cell is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof.

9. The method of claim 5, wherein the PSMA-expressing tumor or cell comprises a benign lesion or tissue.

10. The method of claim 9, wherein the benign lesion or tissue is selected from the group consisting of an endometrium, a schwannoma, and Barrett's esophagus.

11. The method of claim 5, wherein the compound of formula (I) treats the PSMA-expressing tumor or cell by targeting adjacent or nearby cells which express PSMA.

12. The method of claim 11, wherein the cell comprises a vascular cell undergoing angiogenesis.

13. The method of claim 5, wherein the linker group is selected from the group consisting of $-L_1-$, $-L_2-L_3-$, and $-L_1-L_2-L_3-$, wherein:
$L_1$ is $-NH-(CH_2)_m-[O-CH_2-CH_2-O]_p-(CH_2)_q-C(=O)-$;
$L_2$ is $-NH-(CH_2)_s-CH(COOH)-NH-$; and
$L_3$ is $-(O=)C-(CH_2)_t-C(=O)-$;
wherein m, p, q, s, and t are each integers selected from the group consisting of 1, 2, 3, 4, 5, and 6.

14. The compound of claim 1, wherein the linker group is selected from the group consisting of $-L_1-$, $-L_2-L_3-$, and $-L_1-L_2-L_3-$, wherein:
$L_1$ is $-NH-(CH_2)_m-[O-CH_2-CH_2-O]_p-(CH_2)_q-C(=O)-$;
$L_2$ is $-NH-(CH_2)_s-CH(COOH)-NH-$; and
$L_3$ is $-(O=)C-(CH_2)_t-C(=O)-$;
wherein m, p, q, s, and t are each integers selected from the group consisting of 1, 2, 3, 4, 5, and 6.

* * * * *

UNITED STATES PATENT AND TRADEMARK OFFICE
CERTIFICATE OF CORRECTION

Page 1 of 1

PATENT NO. : 10,232,058 B2
APPLICATION NO. : 15/029188
DATED : March 19, 2019
INVENTOR(S) : Martin G. Pomper, Ronnie Mease and Ying Chen It is certified that error appears in the above-identified patent and that said Letters Patent is hereby corrected as shown below:

In the Specification

In Column 1, Line 16, insert:
--This invention was made with government support under CA134675, awarded by the National Institutes of Health. The government has certain rights in the invention.--

Signed and Sealed this
Twenty-second Day of December, 2020

Andrei Iancu
*Director of the United States Patent and Trademark Office*